United States Patent [19]
Taylor et al.

[11] Patent Number: 6,150,573
[45] Date of Patent: Nov. 21, 2000

[54] CONCURRENT PRODUCTION OF TRICHLOROETHANE ISOMERS

[75] Inventors: Tommy G. Taylor, Lake Charles; J. Douglas Mansell, Sulphur; John P. Shamburger, Lake Charles; Mark E. Woodyear, Sulfur, all of La.

[73] Assignee: PPG Industries Ohio, Inc., Cleveland, Ohio

[21] Appl. No.: 08/369,207

[22] Filed: Jan. 5, 1995

Related U.S. Application Data

[62] Division of application No. 08/204,573, Mar. 1, 1994, Pat. No. 5,382,727, which is a division of application No. 08/055,498, Apr. 29, 1993, Pat. No. 5,315,052.

[51] Int. Cl.[7] ............................. C07C 17/38; C07C 17/10
[52] U.S. Cl. ............................................. 570/262; 570/252
[58] Field of Search ..................................... 570/262, 252

[56] References Cited

U.S. PATENT DOCUMENTS

| | | | |
|---|---|---|---|
| 3,658,657 | 4/1972 | Bursack et al. | 570/262 |
| 3,919,337 | 11/1975 | Gordon et al. | 570/252 |
| 4,948,479 | 8/1990 | Brooks et al. | 204/158 |

OTHER PUBLICATIONS

Robert T. Morrison et al, *Organic Chemistry*, 3rd ed., New York University, Allyn and Bacon, Inc., 1979, pp. 197–199, 203–205, 208–211, 242–245, 349, 386–388.

Kirk–Othmer, *Encyclopedia of Chemical Technology*, 3rd ed., vol. 23, John Wiley & Sons, 1983, pp. 868, 884.

*Chemical Abstracts*, vol. 47, Entry 11218f (1953).

*Primary Examiner*—Alan Siegel
*Attorney, Agent, or Firm*—George D. Morris

[57] ABSTRACT

1,1,1-Trichloroethane (viz., methylchloroform) and 1,1,2-trichloroethane are produced in the same reactor by feeding molecular chlorine and chloroethene (viz., vinyl chloride) as well as 1,1-dichloroethane to the reactor. The ratios at which the two trichloroethanes are produced can be easily controlled by controlling the relative ratios of 1,1-dichloroethane and chloroethene introduced to the reactor. The reactions are conducted in the liquid phase in the presence of free radical initiator.

1 Claim, No Drawings

CONCURRENT PRODUCTION OF TRICHLOROETHANE ISOMERS

This is a division of application Ser. No. 08/204,573, filed Mar. 1, 1994 now U.S. Pat. No. 5,382,727, which is a division of application Ser. No. 08/055,498 now U.S. Pat. No. 5,315,052, filed Apr. 29, 1993.

1,1,1-Trichloroethane (viz., methylchloroform) and the isomer of 1,1,1-trichloroethane, namely 1,1,2-trichloroethane, are both items of commerce. Nevertheless, the relative demands for these compounds are constantly changing. This imposes considerable difficulties in the effective use of feed stocks and equipment, especially in a complex, integrated facility for producing chlorohydrocarbons and chlorocarbons.

The present invention is based upon the discovery that 1,1,1-trichloroethane and 1,1,2-trichloroethane can be produced in the same reactor by feeding chloroethene (viz., vinyl chloride) as well as 1,1-dichloroethane to the reactor and, further, that the ratios at which the two trichloroethanes are produced can be easily controlled by controlling the relative ratios of 1,1-dichloroethane and chloroethene introduced to the reactor. Accordingly, in a method for conducting liquid phase chlorination wherein: (a) 1,1-dichloroethane and molecular chlorine are introduced to a reactor containing a liquid phase reaction mixture which comprises free radical initiator; and (b) organic reaction product comprising 1,1,1-trichloroethane is removed from the reactor; the invention is the improvement wherein: (c) chloroethene is introduced to the reactor; (d) the organic reaction product also comprises 1,1,2-trichloroethane; (e) the molar ratio of the 1,1,2-trichloroethane to the 1,1,1-trichloroethane in the organic reaction product is in the range of from 0.2:1 to 2:1; and (f) the 1,1,1-trichloroethane and the 1,1,2-trichloroethane together constitute at least 40 percent by weight of the organic reaction product.

There are many advantages to be realized in conducting both chlorinations in the same equipment. Capital expenditures for new equipment are reduced because separate reactors to produce the trichloroethane compounds are not needed. Operating costs are reduced because there is no longer a need to shut down or uneconomically curtail operation of the reactor producing the trichloroethane isomer temporarily in low demand.

1,1,1-Trichloroethane is produced commercially by reacting 1,1-dichloroethane and molecular chlorine in the liquid phase and in the presence of free radical initiator. The addition of molecular chlorine to chloroethene in the liquid phase to produce 1,1,2-trichloroethane is known; the reaction may proceed by an ionic path when a metal catalyst such as $FeCl_3$ is used, or by a radical path. See, for example, Kirk-Othmer *Encyclopedia of Chemical Technology*, third edition, volume 23, John Wiley & Sons, New York (1983), page 868, and *Chemical Abstracts*, volume 47, American Chemical Society, Columbus Ohio (1953), column 11218f, abstracting JP 26[1951]-6873. It was by no means clear, however, that the introduction of significant amounts of chloroethene to a reactor producing 1,1,1-trichloroethane would function properly. For example, it was known that the rate of chlorination of chloroethene is about 35 to 100 times the rate of chlorination of 1,1-dichloroethane but it was unknown whether the chloroethene would preferentially utilize free radicals to an extent that the chlorination of 1,1-dichloroethane would be quenched or unacceptably reduced. It was known that the rate of chlorination of 1,1,2-trichloroethane to form tetrachloroethanes is nearly 7 times the rate of chlorination of 1,1,1-trichloroethane to form 1,1,1,2-tetrachloroethane, but it was unknown whether increasing the concentration of 1,1,2-trichloroethane in the reaction mixture would give rise to unacceptable increases in the production of tetrachloroethanes, pentachloroethane, and/or hexachloroethane (collectively referred to as "heavies"). It was also unknown whether the chloroethene would polymerize in the free radical environment rather than be chlorinated to 1,1,2-trichloroethane. In view of these and other uncertainties, the discovery that both trichloroethane isomers can be produced in substantial and highly variable quantities in the same reactor without incurring an untowardly increase in heavies production, is surprising.

Any known liquid phase reactor can be used in the practice of the invention. Preferably the reactor is of a type conventionally used for the production of 1,1,1-trichloroethane. It is equipped with inlets for the reactants, an outlet for removal of gaseous hydrogen chloride, an outlet for removal of organic reaction product, and conventional means for regulating the temperature of the reaction mixture. Additional equipment such as an agitator, a vent condenser, pumps, heat exchangers, and the like may be employed as desired.

In practicing the process, 1,1-dichloroethane, chloroethene, molecular chlorine, and free radical initiator are introduced to the reactor which contains a liquid reaction mixture. The reactants may be introduced as separate streams or two or more of the reactants may be combined prior to introduction.

The molar ratio of the chloroethene to the 1,1-dichloroethane introduced to the reactor may vary widely. In most instances, however, the molar ratio of the chloroethene to the 1,1-dichloroethane introduced to the reactor is in the range of from 0.03:1 to 0.8:1. Often the molar ratio is in the range of from 0.05:1 to 0.75:1. From 0.1:1 to 0.7:1 is preferred.

In many cases only a portion of the molecular chlorine introduced is available for the desired chlorinations. This may be due to a variety of causes such as undesired side reactions and loss through the various outlets. It may be seen that the availability of chlorine atoms for the desired chlorinations is a factor to be considered in choosing the relative proportions of molecular chlorine and organic feedstock to be used in conducting the reactions. Other factors to be considered include the degree to which the organic feed stock is to be chlorinated and the quantities and identities of other organic compounds, if any, which will be chlorinated. In general, sufficient molecular chlorine should be introduced to the reactor to accomplish the desired degree of chlorination of the feedstock. Usually, but not necessarily, the ratio of the moles of molecular chlorine to the sum of the moles of chloroethene and the moles of 1,1-dichloroethane introduced to the reactor is in the range of from 0.3:1 to 2.5:1. Often the ratio is in the range of from 0.4:1 to 2:1. From 0.5:1 to 2:1 is preferred.

The free radical initiators that can be used are numerous and widely varied. In most cases, organic free radical initiators are used.

One class of suitable organic free radical initiators comprises the organic peroxygen-containing free radical initiators. This class may be divided into a large number of subclasses, some of which are as follows:

Peroxides, exemplified by diethyl peroxide, di-tert-butyl peroxide [CAS 110-05-4], n-butyl 4,4-bis(tert-butylperoxy) valerate, 1,1-bis(tert-butylperoxy)-3,3,5-trimethylcyclohexane, bis-tert-butyl peroxides of diisopropylbenzene, dicumyl peroxide [CAS-80-43-3], 2,5-dimethyl-2,5-bis(tert-butylperoxy)hexane [CAS 78-63-7], and 2,5-dimethyl-2,5-bis(tert-butylperoxy)-3-hexyne [CAS 1068-27-5].

Hydroperoxides exemplified by methyl hydroperoxide, tert-butyl hydroperoxide [CAS 75-91-2], cumyl hydroperoxide [CAS 80-15-9], 2,5-dimethyl-2,5-dihydroperoxyhexane [CAS 3025-88-5], p-menthanehydroperoxide [CAS 80-47-7], and diisopropylbenzene hydroperoxide [CAS 98-49-7].

Ketone peroxides, exemplified by methyl ethyl ketone peroxide, methyl isobutyl ketone peroxide, cyclohexanone peroxide, 2,4-pentanedione peroxide, the 1,2,4,5-tetraoxacyclohexanes, and the 1,2,4,5,7,8-hexaoxacyclononanes.

Aldehyde peroxides, exemplified by bis(1-hydroxyheptyl) peroxide.

Diperoxyketals, exemplified by 2,2-bis(tert-butylperoxy) butane [CAS 2167-23-9], ethyl 3,3-bis(tert-butylperoxy) butyrate [CAS 55794-20-2], 1,1-bis(tert-butylperoxy) cyclohexane [CAS 3006-86-8], and 1,1-bis(tert-butylperoxy)-3,3,5-trimethylcyclohexane [CAS 6731-36-8].

Diacyl peroxides, exemplified by diacetyl peroxide [CAS 110-22-5], dibenzoyl peroxide [CAS 94-36-0], dicaprylyl peroxide, bis(4-chlorobenzoyl) peroxide, didecanoyl peroxide, bis(2,4-dichlorobenzoyl) peroxide [CAS 133-14-2], diisobutyryl peroxide [CAS 3437-84-1], diisononanoyl peroxide, dilauroyl peroxide [CAS 105-74-8], dipelargonyl peroxide, dipropionyl peroxide, and bis(3-carboxylpropionyl) peroxide.

Peroxycarboxylic acids, exemplified by peroxyacetic acid.

Peroxyesters, exemplified by tert-butyl peroxyacetate [CAS 107-71-1], methyl peroxyacetate, tert-butyl peroxybenzoate [CAS 614-45-9] tert-butyl peroxy(2-ethylhexanonate) [CAS 3006-82-4], tert-butyl peroxyisobutyrate, tert-butyl peroxypivalate, 2,5-dimethyl-2,5-bis(benzoylperoxy)hexane [CAS 618-77-1], tert-butyl peroxy(2-ethylbutyrate), 2,5-dimethyl-2,5-bis(2-ethylhexanoylperoxy)hexane [CAS 13052-09-0], di-tert-butyl diperoxyazelate [CAS 16580-06-6], tert-amyl peroxy (2-ethylhexanoate) [CAS 686-31-7], di-tert-butyldiperoxyphthalate, 0,0-tert-butyl hydrogen monoperoxymaleate, dimethyl peroxyoxalate, di-tert-butyl diperoxyoxalate, and tert-butyl peroxyneodecanoate [CAS 748-41-4].

Peroxycarbonates, exemplified by tert-butylperoxy isopropyl carbonate.

Peroxydicarbonates, exemplified by diisopropyl peroxydicarbonate [CAS 105-64-6], di-sec-butyl peroxydicarbonate, di-n-propyl peroxydicarbonate [CAS 16066-38-9], di(2-ethylhexyl) peroxydicarbonate, dicyclohexyl peroxydicarbonate [CAS 1561-49-5], and dicetyl peroxydicarbonate [CAS 26322-14-5].

Another class of suitable organic free radical initiators comprises the organic azo-nitrile initiators, of which there are many. Examples of suitable azo-nitrile initiators include 2,2'-azobis(2-methylpropanenitrile) [CAS 78-67-1], 2,2'-azobis(2-methylbutanenitrile) [CAS 13472-08-7], 2,2'-azobis(2,4-dimethylpentanenitrile) [CAS 4419-11-8], 2,2'-azobis(4-methoxy-2,4-dimethylpentanenitrile) [CAS 15545-97-8], 1,1'-azobis(cyclohexanecarbonitrile) [CAS 2094-98-6], 4.4'-azobis(4-cyanopentanoic acid) [CAS 2638-94-0], 2,2'-azobis(2-methylpentanenitrile), 2,2'-azobis(2,3-dimethylbutanenitrile), 2,2'-azobis(2-methylhexanenitrile), 2,2'-azobis(2,3-dimethylpentanenitrile), 2,2'-azobis(2,3,3-trimethylbutanenitrile), 2,2'-azobis(2,4,4-trimethylpentanenitrile), 2,2'-azobis(2-methyl-3-phenylpropanenitrile), 2,2'-azobis(2-cyclohexylpropanenitrile), 1,1'-azobis (cycloheptanecarbonitrile),1,1'-azobis(cyclooctanecarbonitrile), 1,1'-azobis(cyclodecanecarbonitrile), 2-(tert-butylazo)-4-methoxy-2,4-dimethylpentanenitrile [CAS 55912-17-9], 2-(tert-butylazo)-2,4-dimethylpentanenitrile [CAS 55912-18-0], 2-(tert-butylazo)-2-methylpropanenitrile [CAS 25149-46-6], 2-(tert-butylazo)-2-methylbutanenitrile [CAS 52235-20-8], 1-(tert-amylazo) cyclohexanecarbonitrile [CAS 55912-19-1], 1-(tert-butylazo)cyclohexanecarbonitrile [CAS 25149-47-7], and 2-[(1-chloro-1-phenylethyl)azo]-2-phenylpropanenitrile.

It is believed that many inorganic free radical initiators and metallic organic free radical initiators are suitable for use in the present invention. Examples of inorganic free radical initiators include sodium peroxide [CAS 1313-60-6], lithium peroxide [CAS 12031-80-0], potassium peroxide [CAS 17014-71-0], magnesium peroxide [CAS 14452-57-4], calcium peroxide [CAS 1305-79-9], strontium peroxide [CAS 1314-18-7], barium peroxide [CAS 1304-29-6], the sodium peroxyborates, sodium carbonate sesqui (peroxyhydrate) [CAS 15630-89-4], disodium peroxydicarbonate [CAS 3313-92-6], dipotassium peroxydicarbonate [CAS 589-97-9], monosodium peroxymonocarbonate [CAS 20745-24-8], monopotassium peroxymonocarbonate [CAS 19024-61-4], peroxymonophosphoric acid [CAS 13598-52-2], peroxydiphosphoric acid [CAS 13825-81-5], tetrapotassium peroxydiphosphate [CAS 15593-49-4], tetrasodium pyrophosphate bis[peroxyhydrate] [CAS 15039-07-3], peroxymonosulfuric acid [CAS 7722-86-3], oxone peroxymonosulfate [CAS 37222-66-5], peroxydisulfuric acid [CAS 13445-49-3], diammonium peroxydisulfate [CAS 7727-54-0], dipotassium peroxydisulfate [CAS 7727-21-1], disodium peroxydisulfate [CAS 7775-27-1], and zinc peroxide [CAS 1314-22-3]. Examples of metallic organic free radical initiators include diethyloxyaluminum tert-cumyl peroxide [CAS 34914-67-5], tri-tert-butyl perborate [CAS 22632-09-3], tert-butyl triethylgermanium peroxide [CAS 26452-74-4], dioxybis[triethylgermane] [CAS 58468-05-6], (tert-butyldioxy)triethylplumbane [CAS 18954-12-6], 00-tert-butyl dimethyl phosphorperoxoate [CAS 18963-64-9], tetrakis[tert-butyl] peroxysilicate [CAS 10196-46-0], dioxybis[trimethylsilane] [CAS 5796-98-5], (tert-butyldioxy)trimethylsilane [CAS 3965-63-7], dioxybis [triethylstannane] [CAS 4403-63-8], and (tert-butyldioxy) trimethylstannane [CAS 20121-56-6].

Other examples of free radical initiators are given in *Kirk-Othmer Encyclopedia of Chemical Technology*, third edition, volume 17, pages 1–90 (1982).

The amount of free radical initiator present in the liquid reaction mixture during the reaction is susceptible to very wide variation. The amount introduced depends upon many factors including, but not limited to: the identity and activity of the initiator; the composition of the organic feedstock; and the presence, identities, and concentrations, if any, of free radical poisons or inhibitors. In general the free radical initiator should be present in the liquid reaction mixture in at least an initiating amount. The minimum and maximum amounts are not limited by any theory, but by practical convenience. Since initiator deactivation is believed to proceed in at least some degree as the chlorination progresses and since it is difficult to ascertain how much active free radical initiator is present at any given instant, the relative proportions of free radical initiator and both chloroethene and 1,1-dichloroethane are best expressed in terms of the weight ratios of these materials introduced to the reaction mixture, although it should be recognized that the amount of active free radical initiator present in the liquid phase reaction mixture is probably less at most times. If initiator deactivation is significant, the addition of free radical initiator may be made intermittently or continuously to remedy the problem. In most instances the ratio of the weight of free radical initiator introduced to the reactor to the sum of the weight of chloroethene and the weight of 1,1-dichloroethane introduced to the reactor is in the range of from 50 to 5000 parts per million parts (ppm). Often the ratio is in the range of from 75 to 3000 ppm. From 100 to 1000 ppm is preferred.

The temperature at which the liquid phase chlorination is conducted may vary considerably. Usually, but not necessarily, the temperature is in the range of from 60° C. to 140° C. A temperature in the range of from 90° C. to 120° C. is preferred.

The pressure at which the liquid phase chlorination is conducted may vary widely. It may be subatmospheric, ambient atmospheric, or superatmospheric. In most cases it is at about ambient atmospheric pressure or somewhat higher. In many instances the pressure is in the range of from 0 to 1400 kilopascals, gauge. Often the pressure is in the range of from 100 to 1000 kilopascals, gauge. Preferably the pressure is in the range of from 340 to 850 kilopascals, gauge.

Hydrogen chloride is removed from the reactor, usually as a gas.

Organic reaction product is removed from the reactor. In most instances the organic reaction product is removed as a liquid as is preferred, but it may be vaporized and removed as a gas. Some may be removed as a liquid and some may be removed as a gas.

The molar ratio of the 1,1,2-trichloroethane to the 1,1,1-trichloroethane in the organic reaction product is in the range of from 0.2:1 to 2:1. Frequently the molar ratio is in the range of from 0.25:1 to 1.5:1. From 0.3:1 to 1.2:1 is preferred.

The 1,1,1-trichloroethane and the 1,1,2-trichloroethane together constitute at least 40 percent by weight of the organic reaction product. Often the 1,1,1-trichloroethane and the 1,1,2-trichloroethane constitute at least 45 percent by weight of the organic reaction product. At least 50 percent is preferred.

Although the preferred mode of operation is continuous, it will be appreciated that the liquid phase chlorination can be conducted semi-batchwise or semi-continuously.

The organic reaction product removed from the reactor may be dealt with as desired. In most cases it is forwarded to a purification system where the desired components are recovered as purified product compounds. The purification system usually comprises a train of distillation columns. In a preferred purification system, the organic reaction product removed from the reactor is forwarded to a first distillation column. An overhead stream chiefly comprising unreacted 1,1-dichloroethane is removed from or near the top of the first distillation column and is recycled to the reactor. A bottoms stream from the first distillation column comprising 1,1,1-trichloroethane, 1,1,2-trichloroethane, 1,2-dichloroethane, and heavies is removed from or near the bottom of the first distillation column and is forwarded to a second distillation column. An overhead stream predominately comprising 1,1,1-trichloroethane and some 1,2-dichloroethane is removed from or near the top of the second column. A bottoms stream chiefly comprising 1,1,2-trichloroethane and heavies is removed from or near the bottom of the second distillation column and is forwarded for further purification.

The 1,2-dichloroethane which is present in the overhead of the second distillation column is present in the organic reaction product as an impurity introduced in the organic feedstock and/or produced as a byproduct in the reactor. The presence of 1,2-dichloroethane in the overhead is particularly undesirable because it is not easily separated from 1,1,1-trichloroethane by simple distillation.

An improvement to the basic method of the invention not only reduces the amount of 1,2-dichloroethane present in overhead from the second distillation column, but results in chlorination of some of the 1,2-dichloroethane to form additional quantities of 1,1,2-trichloroethane which is a desirable coproduct. The improvement comprises separating the reaction product from the reactor into streams including a first stream comprising chiefly 1,1,1-trichloroethane and a contaminating amount of 1,2-dichloroethane, and a second stream comprising chiefly 1,1,2-trichloroethane; and recycling a portion of the first stream to the reactor. The improvement is based upon the recognition that the rate at which 1,2-chloroethane is chlorinated to 1,1,2-trichloroethane is nearly 27 times the rate at which 1,1,1-trichloroethane is chlorinated to unsymmetrical-tetrachloroethane. Only a small amount of the 1,1,1-trichloroethane in the recycled stream is chlorinated to unsymmetrical-trichloroethane.

The amount of 1,2-dichloroethane in the first stream may vary widely. Usually the 1,2-dichloroethane is present in the first stream in an amount in the range of from 0.005 to 0.5 percent by weight. Often it is present in an amount in the range of from 0.01 to 0.3 percent by weight. From 0.02 to 0.2 percent by weight is preferred.

The weight fraction of the first stream which is recycled can vary considerably. In most cases the fraction of the first stream which is recycled to the reactor is in the range from 1 to 95 percent by weight. Often it is in the range of from 5 to 90 percent by weight. From 10 to 80 percent by weight is preferred.

Recycling a portion of the second stream is especially beneficial when chloroethene is introduced to the reactor, nevertheless recycle is useful in any process for producing 1,1,1-trichloroethane from 1,1-dichloroethane where it is desired to reduce the concentration of a contaminating amount of 1,2-dichloroethane in the product. Accordingly, in a method for conducting liquid phase chlorination wherein: (a) 1,1-dichloroethane and molecular chlorine are introduced to a reactor containing a liquid phase reaction mixture which comprises free radical initiator; and (b) organic reaction product comprising 1,1,1-trichloroethane, 1,2-dichloroethane, and 1,1,2-trichloroethane is removed from the reactor; another embodiment of the invention is the improvement comprising: (c) separating the organic reaction product from the reactor into streams including a first stream comprising chiefly 1,1,1-trichloroethane and a contaminating amount of 1,2-dichloroethane, and a second stream comprising chiefly 1,1,2-trichloroethane; and (d) recycling a portion of the first stream to the reactor. The above discussions in respect of chlorination conditions is applicable to this embodiment. The amount of molecular chlorine used should be sufficient to reduce the concentration of the 1,2-dichloroethane to the desired level.

Continuing the progression toward generalization, it will be appreciated that chlorinating a composition comprising 1,1,1-trichloroethane and a contaminating amount of 1,2-dichloroethane has general applicability whenever it is desired to reduce the concentration of the 1,2-dichloroethane. Partial or substantially complete removal of the 1,2-dichloroethane is within contemplation. Accordingly, another embodiment of the invention is a method comprising chlorinating a composition comprising chiefly 1,1,1-trichloroethane and a contaminating amount of 1,2-dichloroethane to reduce the concentration of the 1,2-dichloroethane. Molecular chlorine is the chlorination agent generally employed, although others can be used. The above discussion in respect of chlorination conditions is applicable generally. The amount of chlorination agent used should be sufficient to reduce the concentration of the 1,2-dichloroethane to the desired level.

The invention is further described in conjunction with the following examples which are to be considered illustrative rather than limiting, and in which all parts are parts by weight and all percentages are percentages by weight unless otherwise specified.

A liquid phase reaction mixture was established in a reactor equipped with a vented condenser for the removal of hydrogen chloride. Feed materials were continuously introduced and a liquid product stream was continuously removed. The reaction conditions, the identities and rates of the feed materials, and the composition of the liquid product stream under equilibrium conditions are shown in the Examples below. The abbreviation "ND" means none detected.

EXAMPLE 1

Comparative

| Reaction Conditions<br>Temperature 113° C.<br>Pressure 593 kPa, gauge | |
|---|---|
| Feed Rates, parts/hour | |
| 1,1-Dichloroethane | 6.542 |
| Molecular Chlorine | 4.417 |
| 2,2'-Azobis(2-methylpropanenitrile) | 0.000868 |
| Chloroethene | 0 |
| Hydrogen Chloride | 0 |
| Liquid Product Stream Composition, weight percent | |
| 1,1-Dichloroethene | 0.000 |
| 1,2-Dichloroethane | 0.03 |
| 1,1-Dichloroethane | 43.0 |
| 1,1,1-Trichloroethane | 36.0 |
| 1,1,2-Trichloroethane | 13.0 |
| 1,1,1,2-Tetrachloroethane | 5.0 |
| 1,1,2,2-Tetrachloroethane | 3.0 |
| Pentachloroethane | 1.7 |
| Hexachloroethane | 0.08 |
| Chloroethene | ND |

EXAMPLE 2

| Reaction Conditions<br>Temperature 113° C.<br>Pressure 607 kPa, gauge | |
|---|---|
| Feed Rates, parts/hour | |
| 1,1-Dichloroethane | 10.000 |
| Molecular Chlorine | 9.375 |
| 2,2'-Azobis(2-methylpropanenitrile) | 0.00145 |
| Chloroethene | 0.455 |
| Hydrogen Chloride | 0.124 |
| Liquid Product Stream Composition, weight percent | |
| 1,1-Dichloroethene | 0.04 |
| 1,1-Dichloroethane | 37.0 |
| 1,1,1-Trichloroethane | 35.0 |
| 1,1,2-Trichloroethane | 16.5 |
| 1,1,1,2-Tetrachloroethane | 6.4 |
| 1,1,2,2-Tetrachloroethane | 4.1 |
| Pentachloroethane | 1.7 |
| Hexachloroethane | 0.08 |
| Chloroethene | ND |

EXAMPLE 3

| Reaction Conditions<br>Temperature 113° C.<br>Pressure 607 kPa, gauge | |
|---|---|
| Feed Rates, parts/hour | |
| 1,1-Dichloroethane | 6.667 |
| Molecular Chlorine | 7.625 |
| 2,2'-Azobis(2-methylpropanenitrile) | 0.000940 |
| Chloroethene | 1.050 |
| Hydrogen Chloride | 0.290 |
| Liquid Product Stream Composition, weight percent | |
| 1,1-Dichloroethene | 0.03 |
| 1,1-Dichloroethane | 26.0 |
| 1,1,1-Trichloroethane | 43.0 |
| 1,1,2-Trichloroethane | 17.0 |
| 1,1,1,2-Tetrachloroethane | 4.6 |
| 1,1,2,2-Tetrachloroethane | 2.1 |
| Pentachloroethane | 0.1 |
| Hexachloroethane | 0.08 |
| Chloroethene | 0.02 |

EXAMPLE 4

| Reaction Conditions<br>Temperature 117° C.<br>Pressure 607 kPa, gauge | |
|---|---|
| Feed Rates, parts/hour | |
| 1,1-Dichloroethane | 3.750 |
| Molecular Chlorine | 9.000 |
| 2,2'-Azobis(2-methylpropanenitrile) | 0.00116 |
| Chloroethene | 2.292 |
| Hydrogen Chloride | 0.625 |
| Liquid Product Stream Composition, weight percent | |
| 1,1-Dichloroethene | 0.0 |
| 1,1-Dichloroethane | 20.0 |
| 1,1,1-Trichloroethane | 33.0 |
| 1,1,2-Trichloroethane | 25.5 |
| 1,1,1,2-Tetrachloroethane | 11.0 |
| 1,1,2,2-Tetrachloroethane | 8.5 |
| Pentachloroethane | 3.0 |
| Hexachloroethane | 0.1 |
| Chloroethene | ND |

Although the present invention has been described with reference to specific details of certain embodiments thereof, it is not intended that such details should be regarded as limitations upon the scope of the invention except insofar as they are included in the accompanying claims.

What is claimed is:

1. A method comprising chlorinating a composition comprising chiefly 1,1,1-trichloroethane and a contaminating amount of 1,2-dichloroethane to reduce the concentration of said 1,2-dichloroethane.

* * * * *